US005343713A

United States Patent [19]

Okabe et al.

[11] Patent Number: 5,343,713

[45] Date of Patent: Sep. 6, 1994

[54] ACTIVE NOISE CONTROL APPARATUS FOR THREE-DIMENSIONAL SPACE

[75] Inventors: Shinya Okabe, Shimizu; Shinichi Shimode, Minori; Ryouji Sato; Masamichi Hanada, both of Shimizu; Takao Senshu; Hirokiyo Terada, both of Shizuoka; Minetoshi Izushi, Shimizu; Hiroshi Takenaka, Shimizu; Masahiro Ito, Shimizu, all of Japan

[73] Assignee: Hitachi, Ltd., Tokyo, Japan

[21] Appl. No.: 19,708

[22] Filed: Feb. 19, 1993

[30] Foreign Application Priority Data

Feb. 19, 1992 [JP] Japan .................................. 4-032029
Sep. 21, 1992 [JP] Japan .................................. 4-250942

[51] Int. Cl.[5] ........................ A61F 11/06; F25D 19/00
[52] U.S. Cl. ........................................ 62/296; 181/206; 381/71; 454/206
[58] Field of Search ........................... 62/296; 417/312; 381/71, 94; 181/206; 454/206

[56] References Cited

U.S. PATENT DOCUMENTS 5,125,241 6/1992 Nakanishi et al. .................... 62/296
5,216,722 6/1993 Popovich .............................. 381/71

*Primary Examiner*—William E. Wayner
*Attorney, Agent, or Firm*—Antonelli, Terry, Stout & Kraus

[57] ABSTRACT

An active noise control system for a three-dimensional space, including noise detecting means, sound generating means, noise control effect detecting means and a control device consisting of a phase of a wave signal fed from the noise detecting means wherein a plurality of noise control effect detecting means and sound generating means are disposed at a distance shorter than a wavelength of the noise to be controlled, and input signals of the respective sound generating means and output signals of the respective noise control effect detecting means are fed through filters, separately, to control the sound for active noise control. In case of an air conditioner, the noise control effect detecting means are disposed at positions where an air stream flowing through the air conditioner is not obstructed thereby.

37 Claims, 16 Drawing Sheets

$$H_0 = \frac{V_3}{V_2}$$

ACTIVE NOISE CONTROL APPARATUS FOR THREE-DIMENSIONAL SPACE

BACKGROUND OF THE INVENTION

1. Field of the Inventions

The present invention relates to an active noise control apparatus for a three-dimensional space and, more particularly, to an active noise control apparatus for effecting an active noise control apparatus at local areas in a three-dimensional area, such active noise control apparatus is suitable to suppress noises caused by periodic sound or random sound, such as electromagnetic noise, blade tone noise or the like of a fan disposed at an inlet port of an air conditioner in an active noise control manner in a three-dimensional space.

2. Description of the Related Art

Heretofore, in order to reduce noises of an air conditioner or the like, a passive noise control method has been adopted. The passive noise control method includes a noise source control by reducing a vibration which forms a noise source of an air conditioner, a noise absorption in which a noise produced is absorbed by a noise absorbing material, a noise shielding in which a noise produced is prevented from being transmitted to another area, or the like. Recently, an active noise control method has been developed. According to the active noise control method, a noise produced is controlled by another sound which has a same wavelength (same frequency) and same amplitude as those of the noise to be controlled. The active noise control method has come into practical use in the field where a noise is transmitted in a one dimensional space such as in a duct of an air conditioner.

The fundamental concept of the active noise control method itself has been known from about 1936. The active noise control method requires coincidental generation of a sound having a same wavelength (same frequency and same amplitude as those of a noise to be suppressed, which has not been realized until now.

Recently, a digital signal processing art has made a considerable development until it has become possible to generate a sound wave having a same wavelength (same frequency) and same amplitude as those of a noise to be suppressed and thus the active noise control method has become realized.

An example of a conventional active noise control method for a one-dimensional space is illustrated in FIG. 1. The active noise control system as shown in FIG. 1 includes a noise detecting means 1, a sound generating means 2, a noise control effect detecting means 3 and a controller 4. A noise is transmitted from an upstream side (left side in FIG. 1) through a duct (for example, an air conditioner duct) to a downstream side (right side in FIG. 1). The noise is detected by the noise detecting means 1 and is converted into an electric signal, which is fed to the controller 4. The controller 4 acts to analyze the electric signal and feed an output signal to the sound generating means, to effect the active noise control. The sound generating means radiates a sound having an opposite phase to that of the noise into the duct. The noise control effect detecting means 3 acts to detect a noise control effect produced by the sound generating means. The output signal fed to the sound generating means 2 is corrected by feeding back a signal from the noise control effect detecting means 3 to the controller 4, on the basis of the noise control effect, so that the noise is always suppressed at the position of the control effect detecting means 3. Thus, the noise is suppressed at the position of the noise control effect detecting means 3 and the downstream side thereof (the right side in FIG. 1). The controller 4 includes an adaptive filter 4A which can be varied according to an adaptive algorithm 4B by digital signal processing. The controller 4 further includes a fixed filter 5. In order to effect the digital signal processing, an actually measured value of a transfer function Ho, which is defined by a ratio of (a voltage $V_3$ of an output signal from the noise control effect detecting means 3 to the sound generating means 2)/(a voltage $V_2$ of an input voltage from the controller 4 to the sound generating means 2), as shown in FIG. 2, is fed to the fixed filter 5. In an actual measurement, sound signals of M-series are outputted as a white noise from the controller 4 and these sound signals are radiated from the sound generating means 2, while the sound signals are returned from the noise control effect detecting means 3 to the controller 4. The Ho is obtained from these sound signals. Thus, a distance between the sound generating means 2 and the noise control effect detecting means 3, reverberation characteristic in the duct and instrument characteristics of the sound generating means and the noise control effect detecting means are taken into consideration, and these factors can be corrected at the process of noise control.

An interference of sounds radiated into a three-dimensional field is different from that of sounds radiated into a one-dimensional field, in that the active noise control for the three-dimensional space is different from the active noise control for the one-dimensional space. Presuming an ideal state, if a sound generating means was located at the same position with that of a noise source and a sound having a same amplitude and same wavelength as those of the noise was radiated from the sound generating means, a destructing interference of sound waves would occur, so that a noise suppression in the three-dimensional space could be effected. However, in a real state, it is impossible to locate the sound generating means completely at the same position with that of the noise source and, therefore, in the active noise control for the three-dimensional space it is required to locate a plurality of sound generating means near the noise source (each at a distance at least shorter than ½ of a wavelength). In other words, the greater sound control effect can be obtained, as the wavelength of sound is longer (that is, the frequency is lower) and the sound source is smaller. This is because a sound coming from a noise source becomes similar to a non-directional sound coming from a spot source. Conversely, a smaller sound control effect can be obtained as the wavelength of sound is shorter (that is, the frequency is higher) or the sound source is larger, because the noise has directivity.

There are other problems in the active sound control for the three-dimensional space.

FIG. 3 illustrates an active sound control for a three-dimensional field into which sound waves having a same amplitude and same frequency but opposite phases to each other are radiated from two spot sound sources S1 and S2. The spot sound sources S1 and S2 produce sound wave W1 and W2. Solid lines and broken lines of the sound waves W1 and W2 indicate loops and nodes of the sound waves, respectively. In such state, owing to interference of the sound waves having a same amplitude, same frequency and opposite phases to each other, sound decreasing areas A where the two sound waves cancel out with each other and sound increasing area B where the two sound waves add to each other are formed. Accordingly, if one of the sound sources is a noise source and the other sound source is used as a sound generating means for the active noise control system, it is possible to effect the active noise control for the three-dimensional field. The size and the noise control effect of the local area where the active noise control can be effected are in proportion to the wavelength of the sound and, therefore, single or plural noise control effect detecting means, single or plural sound generating means and single or plural noise detecting means are provided, depending upon the position and size of the local area where the noise suppression or noise reduction is to be effected, the frequency of sound and the object of noise reduction, and the arrangement of such noise control effect detecting means, sound generating means and noise detecting means is determined according to the object. It is further required to pay attention to the space of the room, appearance as an interior, cost of each instrument and the like. It is an object of solving such various problems in the active noise control for the three-dimensional space.

Japanese Patent Application Laid-Open No. HEI-2-61450 discloses an air conditioner which includes a first sound receiving means, for receiving a noise produced from a fan or the like, a phase converting means for converting a phase of a waveform received by said first sound receiving means into opposite phase, a sound generating means for converting a waveform signal fed from said phase converting means into a sound, a second sound receiving means for detecting a composite sound in which the sound from said sound generating means is combined with the original noise and control means for discriminating levels of a sound received by said second sound receiving means and a sound received by said first sound receiving means, respectively, to effect level adjustment and phase adjustment, whereby said control means acts to effect noise control of said composite sound received by said second sound receiving means.

This noise control method is not technically unsatisfactory in order to effect the active noise control for the three-dimensional space.

The applicant has proposed an air conditioner which includes an active noise control apparatus for a three-dimensional space, as shown in FIGS. 4 and 5, in which a plurality of sound generating means are arranged near a noise source. FIG. 4 is a perspective view of the air conditioner which is of ceiling mounted type. In order to reduce a low frequency periodic noise, such as blade tone noise, electromagnetic noise on the like, which is radiated to a whole three-dimensional space, by an active noise control method, noise detecting means 1 (blade tone pickup, electromagnetic noise pickup) are disposed near a turbo-fan 6 which forms a noise source, and sound generating means 2*a* and 2*b* and noise control effect detecting means 3*a* and 3*b* are disposed around the turbo-fan 6. The apparatus further includes a controller 4, an air filter 7, a grill 8 and an electrical control box 9.

FIG. 5 illustrates a general control arrangement for effecting active noise control of the air conditioner as shown in FIG. 4.

According to the arrangement as shown in FIGS. 4 and 5, it is only possible to control a noise coming from a noise source which is of a non-directional property and it is difficult to control a noise having relatively high frequency in a three-dimensional space because it is required to control a noise having a directivity.

Furthermore, in the case of the air conditioner of an active noise control type, such problem that an air flow is impeded by sound generating means and other inconvenience tend to occur. It is further required to pay attention to lower the costs of the apparatus and to enable effective use of respective instruments for the active noise control.

OBJECT OF THE INVENTION

It is an object of the present invention to provide an active noise control apparatus which can effectively control a noise of wide frequency range from low frequency to high frequency which is radiated into a three-dimensional space.

It is another object of the present invention to provide an active noise control apparatus which is arranged to be able to select local areas for active sound control at any desired position or positions in a three-dimensional space and which enables selection of numbers and sizes of the local areas for noise control as desired.

SUMMARY OF THE INVENTION

In accordance with an aspect of the present invention there is provided an active noise control apparatus for a three-dimensional space which includes a noise detecting means for detecting a noise radiating from a noise source, a control device for effecting active noise control, a plurality of sound generating means which are arranged at a distance between the respective sound generating means and at a distance from said noise source shorter than $\frac{1}{2}$ of a wavelength of a sound having highest frequency of said noise to be controlled and are arranged to surround said noise source, and a noise control effect detecting means; wherein said control device for active noise control is arranged to radiate, from said sound generating means, a sound wave having an opposite phase to and same sound pressure, same wavelength and same directivity as those of a noise of a high frequency range radiated from said noise source into the three-dimensional space.

In accordance with another aspect of the invention there is provided an active noise control apparatus for a three-dimensional space including a noise detecting means for detecting a noise, a sound radiating means for radiating a sound for effecting an active noise control actions, a noise control effect detecting means disposed at a local area in a noise control, area in the three-dimensional space for noise control to detect a noise in said noise control area, and a control device for controlling the active noise control action, wherein said control device is arranged to effect active noise control in said noise control area by controlling said sound generating means so that a sound for active noise control which has arrived at the noise control area from said sound generating means is adjusted to a sound having an opposite phase to and same sound pressure and same wavelength as those of a noise to be controlled, whereby the noise within the noise control area detected by said noise control effect detecting means becomes minimum, on the basis of output signals of said noise detecting means and said noise control effect detecting means; in which said noise control effect detecting means can be disposed at any desired position, and said control device for active noise control and said noise control effect detecting means are connected together by transmitting means, such as flexible and movable parallel cords, coaxial cable, optical fiber or radio wave.

BRIEF DESCRIPTION OF THE DRAWINGS

FIGS. 6A, 6B and 6C illustrate an air conditioner of a ceiling mounted type according to an embodiment of the present invention, in which FIG. 6A is a perspective view, FIG. 6B is a sectional view and FIG. 6C is a plan view of a grill thereof;

FIGS. 9A and 9B illustrate an air flow in the air conditioner of a ceiling-mounted type, in which FIG. 9A is a sectional view and FIG. 9B is a bottom plan view;

DESCRIPTION OF THE PREFERRED EMBODIMENTS

Now, the invention will be explained in detail, with reference to the accompanying drawings.

Figure 1:
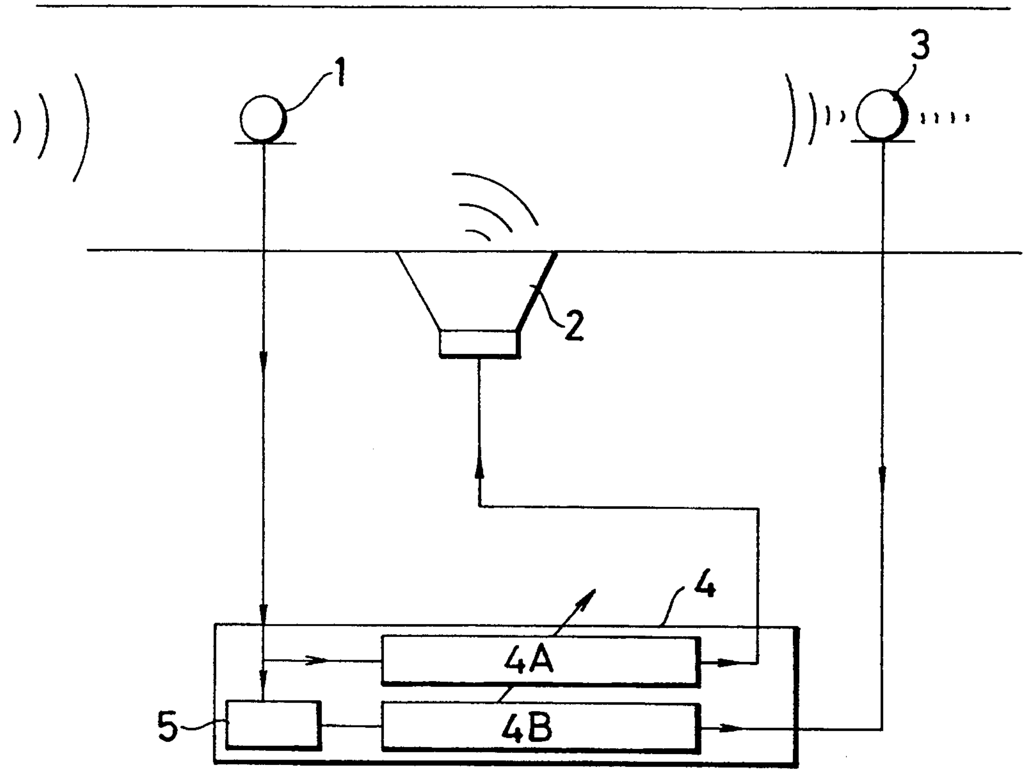
FIG. 1 PRIOR ART
FIG. 1 illustrates an example of a conventional active noise control for a one-dimensional sound wave in a duct.
Figures 2, 3:
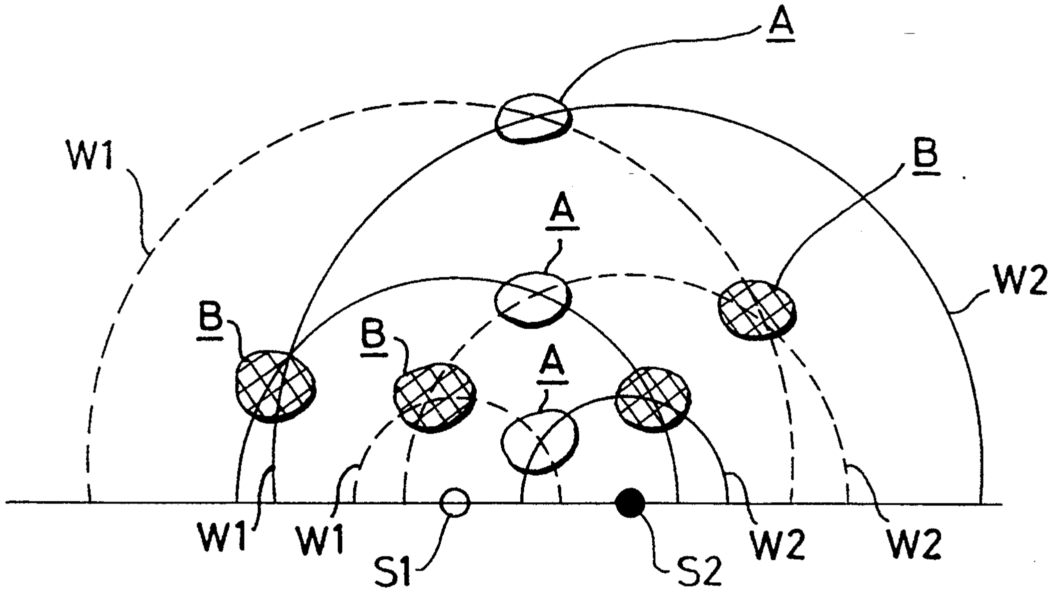
FIG. 2 shows a fixed filter used in the active noise control as shown in FIG. 1.
FIG. 3 illustrates an interference of three-dimensional sounds radiated from two spot sounds radiated from two spot sound sources having opposite phases.
Figure 4:
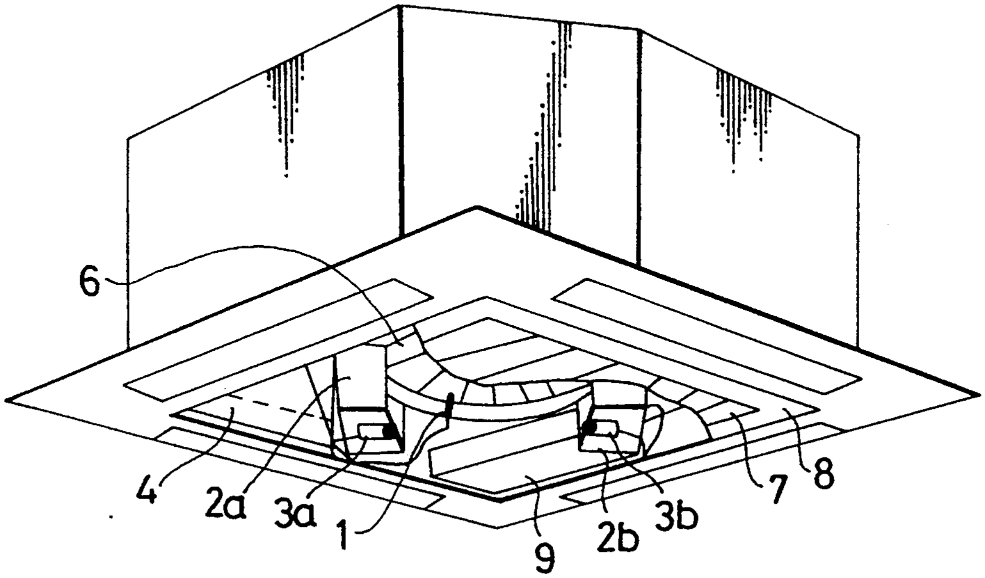
FIG. 4 is a perspective view showing a prior art of an air conditioner of a three-dimensional active noise control type.
Figure 6A:
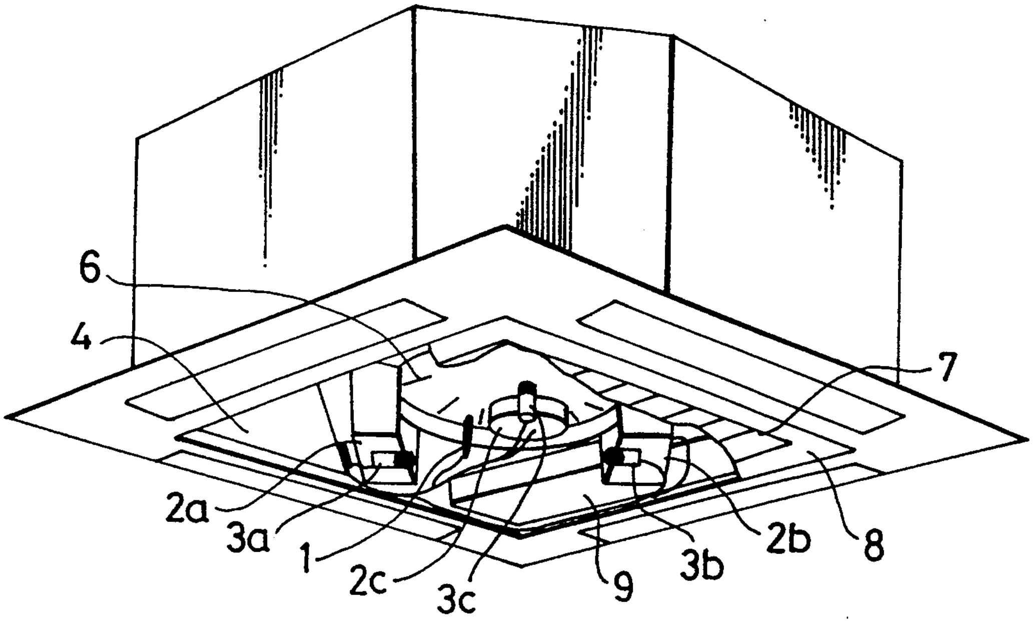
Figure 6B:
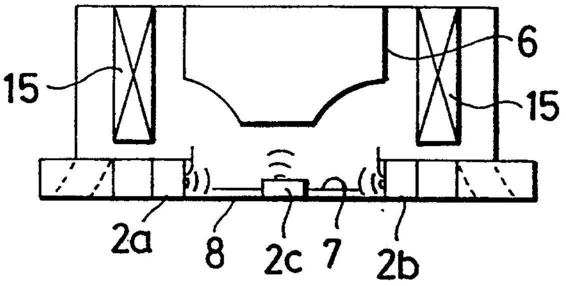
Figure 6C:
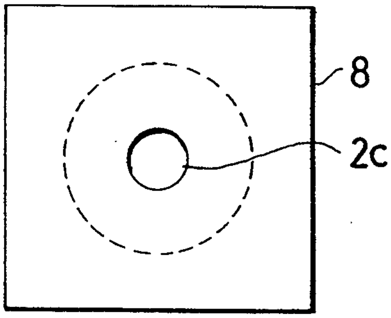

FIGS. 6A, 6B and 6C illustrate an air conditioner according to an embodiment of the present invention, in which FIG. 6A is a perspective view, FIG. 6B is a vertical sectional view and FIG. 6C is a plan view of a grill thereof. In FIGS., 6A, 6B and 6C, the same parts as those shown in FIG. 4 are indicated by the same symbols as used in FIG. 4, and the numeral 15 indicates a heat exchanger. The feature of this embodiment is different from that shown in FIG. 4 by the provision of one additional sound generating means 2C and one additional sound generating means 3C, which are disposed on an inlet grill 8 having an air filter 7, at the position corresponding to a center of the turbo-fan 6.

According to such arrangement, the distance between the respective sound generating means 2*a*, 2*b* and 2*c* is reduced to ½ in the embodiment shown in FIG. 6A, as compared to the arrangement as shown in FIG. 4, so that it becomes possible to effect the active noise control in a wider frequency range, such as two times of the frequency range wherein it is possible to effect the active noise control by the arrangement shown in FIG. 4.

In FIGS., 6A, 6B and 6C, the three sound generating means 2*a*, 2*b* and 2*c* are so arranged that the distances between these sound generating means and the distance between each sound generating means and the turbo-fan 6, which forms the noise source, are shorter than ½ of the wavelength of the noise having maximum frequency noises which are to be controlled, and these sound generating means are disposed so as to surround the turbo-fan 6 which forms the noise source.

Figure 5:
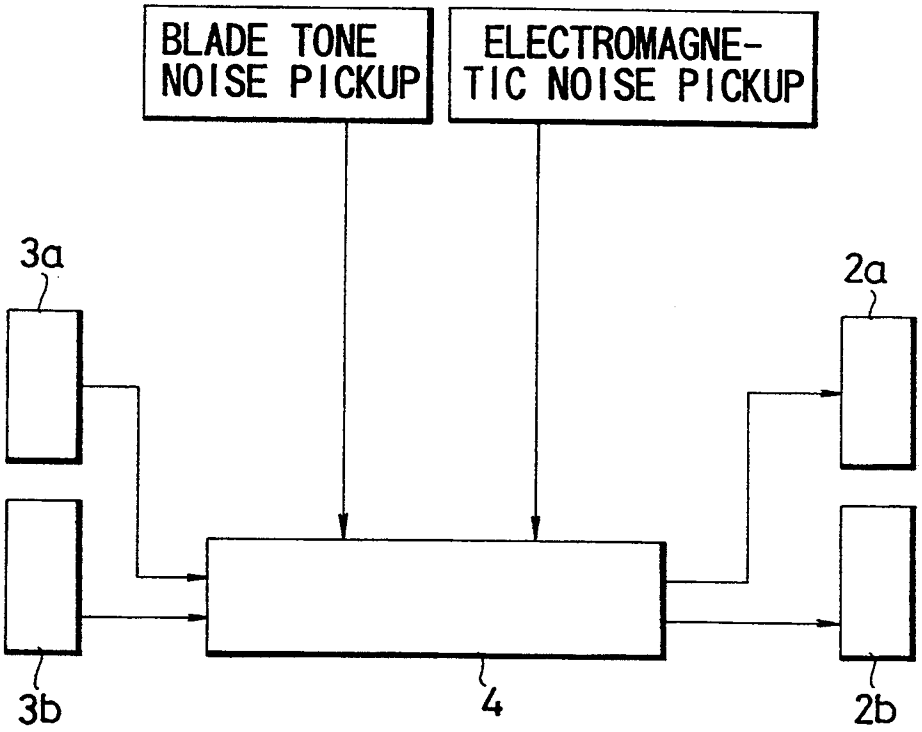
FIG. 5 shows a control arrangement for the active noise control in the air conditioner as shown in FIG. 4.
Figure 7:
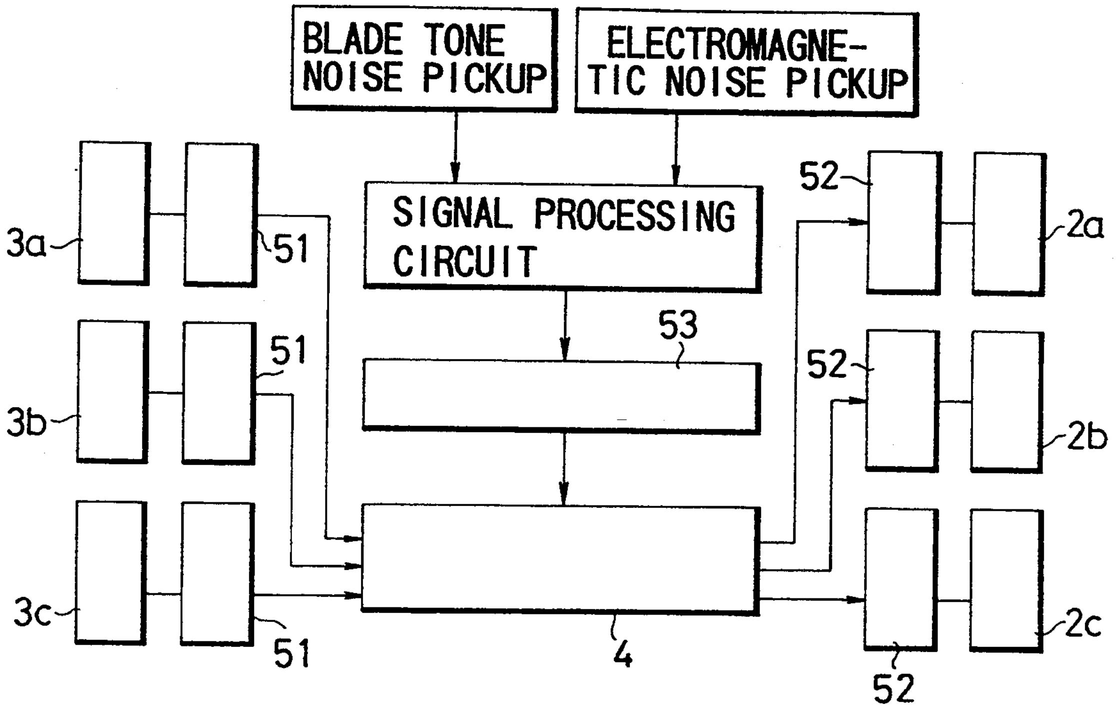
FIG. 7 shows a control arrangement for effecting the active noise control as shown in FIGS. 6A, 6B and 6C.

FIG. 7 shows a control arrangement of the active noise control system for the air controller shown in FIGS. 6A, 6B and 6C. As compared to the control arrangement shown in FIG. 5, in the embodiment of the control arrangement as shown in FIG. 7 fixed filters 51 and 52 are interposed between each of the noise control effect detecting means 3*a*, 3*b* and 3*c* and the controller (phase converting means) 4 and between the controller and each of the sound generating means 2*a*, 2*b* and 2*c*, respectively. These fixed filters 51 and 52 have characteristics which depend upon actually measured values of transfer functions between the noise control effect detecting means 3*a*, 3*b* and 3*c* and a plurality of representative spots set in the three-dimensional space so as to surround the turbo-fan 6, which forms the noise source in the air conditioner, and actually measured values of transfer functions between the sound generating means 2*a*, 2*b* and 2*c* and a plurality of representative spots in the three-dimensional space.

Further, a fixed filter 53, having a characteristic which depends upon actually measured values of transfer functions between the noise detecting means 1 (blade tone noise pickup and electromagnetic noise pickup of the turbo-fan) and representative spots in the three-dimensional space, is interposed between the signal processing circuit and the controller 4. This arrangement enables noise control not only at the positions of the noise control effect detecting means 3*a*, 3*b* and 3*c* but also in the whole area of the three-dimensional space.

Figure 8:
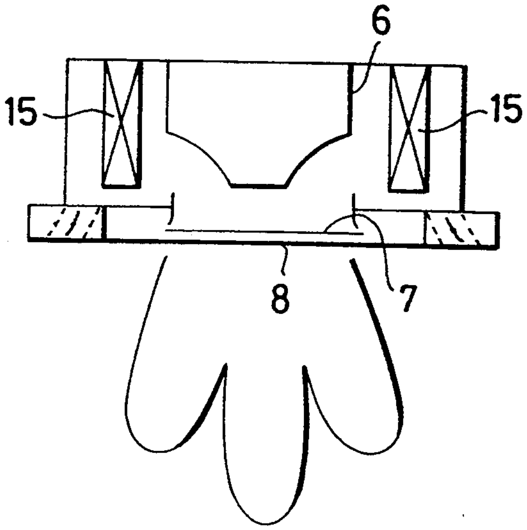
FIG. 8 illustrates a directivity of a noise produced in the air conditioner of a ceiling-mounted type.

FIG. 8 is a sectional view showing the directivity of a noise radiated from an air conditioner of ceiling-mounted type. In case of the air conditioner of ceiling-mounted type as shown in FIG. 6A it is possible to radiate a sound having a directivity which is equal or similar to that shown in FIG. 8, from the sound generating means 2*a*, 2*b* and 2*c* and consequently, it is possible to effect active noise control of a noise having a high frequency which produces the directivity.

Figure 9A:
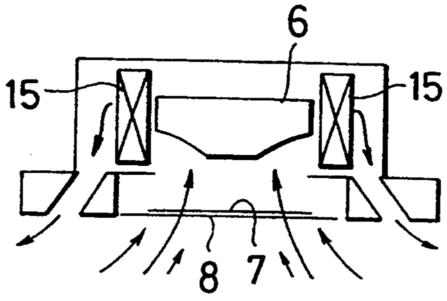
Figure 9B:
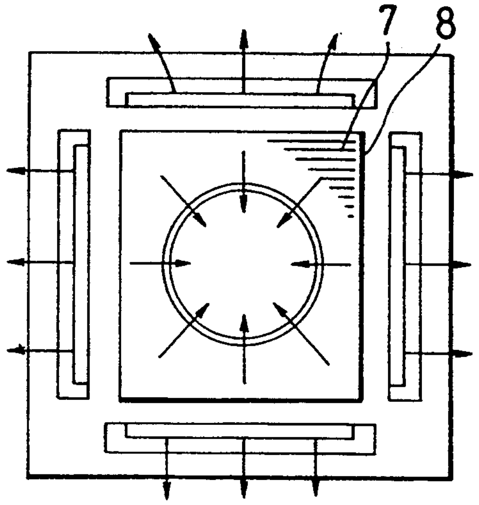

FIGS. 9A and 9B are a sectional view and bottom plan view, respectively, showing air streams flowing through an air conditioner of a ceiling-mounted type. A fewer amount of air flows through a central position of the turbo-fan 6 at the inlet grill 8 having the air filter 7. Accordingly, very small obstruction to the air stream occurs if the sound generating means 2*c* is disposed at the center of the fan 6.

Figure 10:
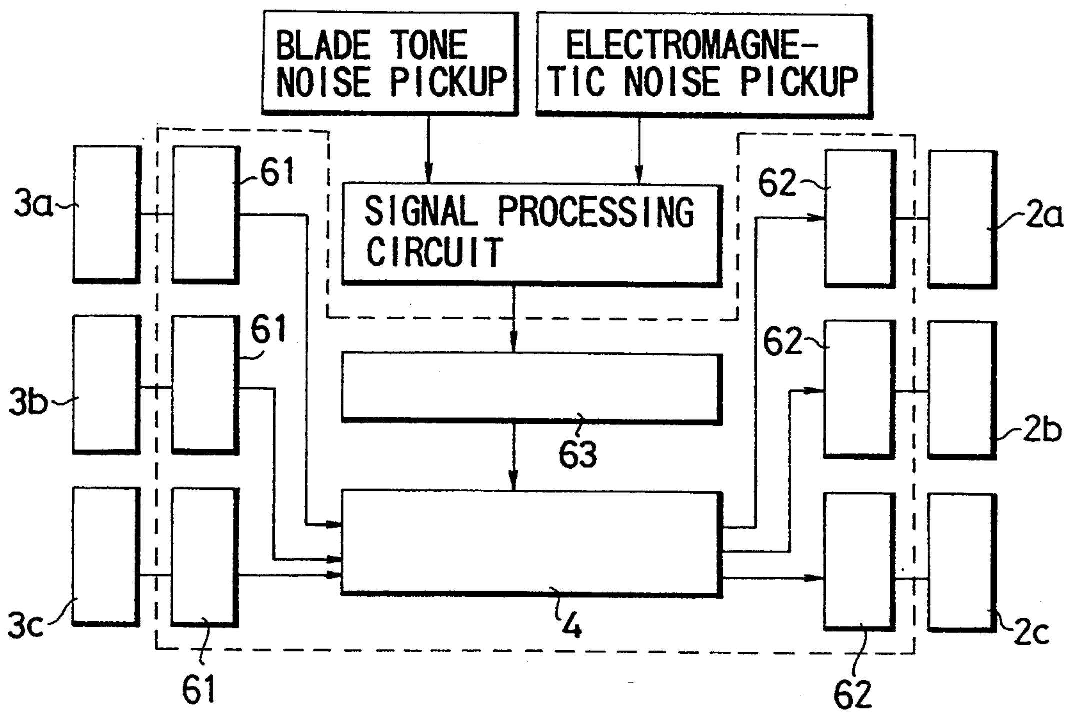
FIG. 10 shows another control arrangement for active noise control in the above embodiment.

In the air conditioner as shown in FIG. 6A a rotation noise (blade tone noise) detecting pickup for a turbo-fan 6 and an electromagnetic noise pickup for a motor for driving the fan are provided as the noise detecting means 1. The controller (phase converter) 4 and the electrical control box 9 are disposed at the positions where easy maintenance operation can be effected. The noise control effect detecting means 3*a*, 3*b* and 3*c* may consist of condenser microphones, which are of low cost and enable easy actual measurement of the transfer function between representative spots in the three-dimensional space by feeding an electric signal reversely into the condenser microphones. FIG. 10 is a diagram showing another control arrangement which can be used instead of the control arrangement shown in FIG. 7. The feature of this arrangement different from that shown in FIG. 7 is that adaptive filters 61, 62 and 63 which make proper variations are used instead of the fixed filters 51, 52 and 53.

The characteristics of the elements shown in a box of broken line in FIG. 10 are determined, from time to time depending upon the mutual relationship therebetween. These adaptive filters control effect detecting means 3*a*, 3*b* and 3*c* and the controller (phase converter) 4, between the sound generating means 2*a*, 2*b* and 2*c* and the controller 4, and between the noise detecting means 1 and the controller 4, respectively. These adaptive filters constantly make variations, respectively, and are determined, depending upon the transfer functions between the noise control effect detecting means 3*a*, 3*b* and 3*c* and the representative spots in the three-dimensional space, the transfer functions between the sound generating means 2*a*, 2*b* and 2*c* and the representative spots in the three-dimensional space and the transfer functions between the noise detecting means 1 and the representative spots in the three-dimensional space. According to such arrangement, it is possible to effect the noise control not only at the positions of the noise control effect detecting means 3*a*, 3*b* and 3*c* but also in the whole area of the three-dimensional space. It is possible to use some fixed filters instead of some adaptive filters, thereby constituting a mixed control arrangement including adaptive filters and fixed filters.

In the control arrangements shown in FIGS. 7 and 10, second to n-th component signals of the output signals of the blade tone noise pickup and the electromagnetic noise pickup are produced in the signal processing circuit, and these component signals are subjected to gain adjustment and then mixed and outputted.

The plurality of noise control effect detecting means 3*a*, 3*b* and 3*c* are disposed at the positions where the noise control effect in the three-dimensional space becomes maximum, that is, the positions where the sound pressure caused by the interference of the sound coming from the noise source and the sounds coming from the sound generating means 2*a*, 2*b* and 2*c* becomes minimum (usually, the positions at the middle between the center of the noise source and each sound generating means). The signal is corrected by passing the signal through the fixed filter or the adaptive filter, whereby the signal becomes equal or similar to a proper signal for the noise control.

Figure 11A:
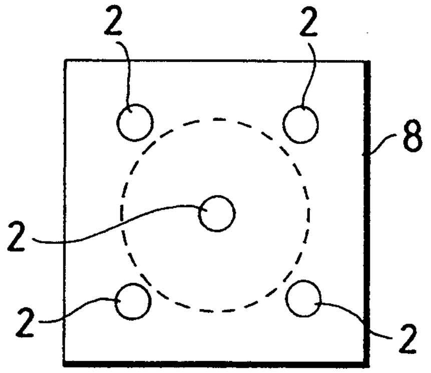
FIGS. 11A, 11B and 11C are plan views of grills, showing some examples of arrangement of a plurality of sound generating means.
Figure 11B:
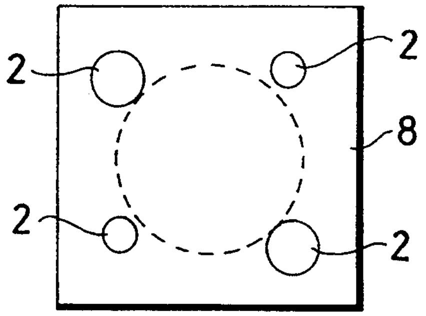
Figure 11C:
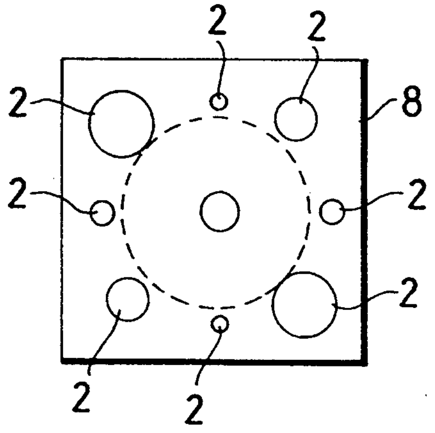

FIGS. 11A, 11B and 11C are bottom plan views of an inlet grill 8 of an air conditioner of a ceiling-mounted type on which a plurality of sound generating means 2 are arranged. Each sound generating means 2 is arranged at the position where an air stream is not obstructed thereby. In these figures, all of the sound generating means are indicated simply by the numeral 2. The size and the position of each sound generating means 2 are determined, depending upon the frequency of sound to be controlled, requirements in space or the like, and the position and the size of the respective sound generating means may be different from each other.

These sound generating means 2 are arranged, in the same manner as in FIG. 6, so that the distance between the respective sound generating means and the distance between each sound generating means and the turbo-fan 6, that is the noise source, are shorter than ½ of the wavelength of the noise having a maximum frequency which is to be controlled.

Figure 12:
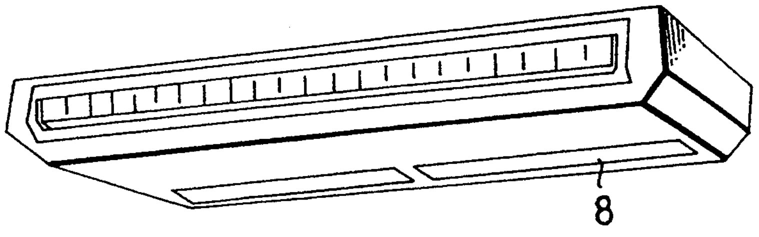
FIG. 12 is a perspective view showing another embodiment of the air conditioner.
Figure 13:
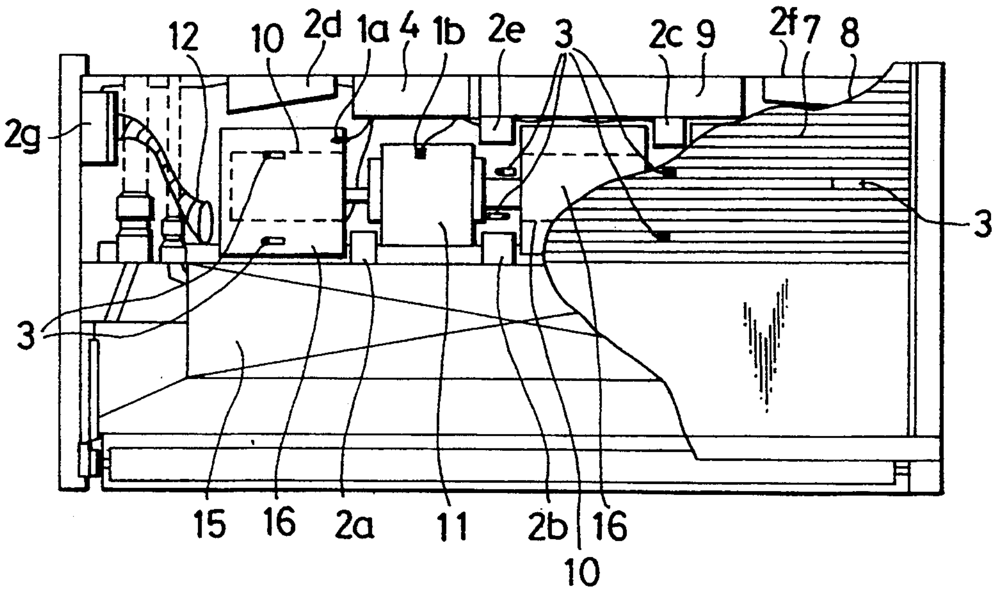
FIG. 13 is a partially broken plan view showing an inside of the embodiment shown in FIG. 12.

FIG. 12 is a perspective view showing another embodiment of the air conditioner according to the present invention. The air conditioner as shown in FIG. 12 has a rotation noise detecting pickup l*a* for a sirocco fan having a casing 16 and an electromagnetic noise detecting pickup 16 for a motor 11 for rotating said fan 10. The air conditioner further has a plurality of sound generating means 2*a*–2*g* and plurality of noise control effect detecting means 3. These plurality of sound generating means 2*a*–2*g* are so arranged that those having different sizes are disposed with suitable gaps between the respective elements of the air conditioner, depending upon the frequency to be controlled, the space requirements or the like, as shown in FIG. 13. For example, one of the sound generating means is disposed between the fan 10 and the motor 11. In case of the sound generating means 2*g*, it is set at a position remote from the noise source such as the sirocco fan 10, the motor 11 or the like, and a sound transmitting tube 12 is used to radiate the sound of the sound generating means from the sound transmitting tube 12 at any desired position. A heat exchanger 15 is provided in the air conditioner. Noise control effect detecting means 3 are disposed at suitable positions on an inlet grill 8 having an air filter 7. The noise control effect detecting means makes use of condenser microphones, with the object of lowering cost and increasing convenience for use. A controller (phase converter) 4 is disposed at a position for effecting easy maintenance, as in the case of the electrical control box 9. These sound generating means 2*a*–2*g* (in the case of 2*g*, the forward end of the sound transmitting means) are arranged so that the distances between the respective sound producing means and the distance between each sound producing means and the noise source, that is the sirocco fan or the motor, are shorter than ½ of the wavelength of the sound having maximum frequency among the noises to be controlled, and they are disposed around the noise source at the positions where the air stream is not obstructed thereby.

Figure 14:
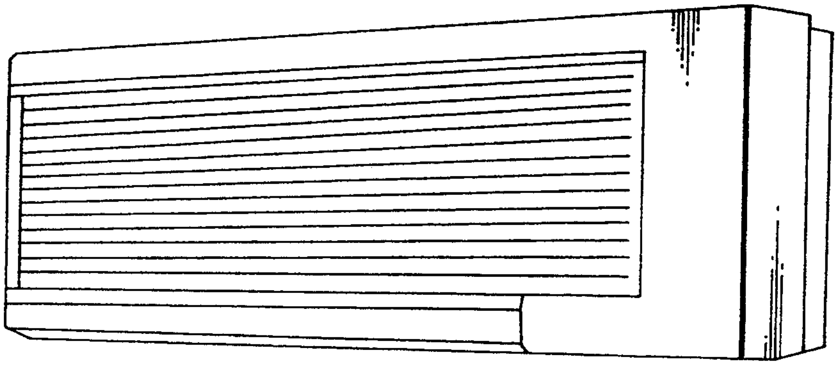
FIG. 14 is a perspective view showing a further embodiment of the air conditioner.
Figure 15:
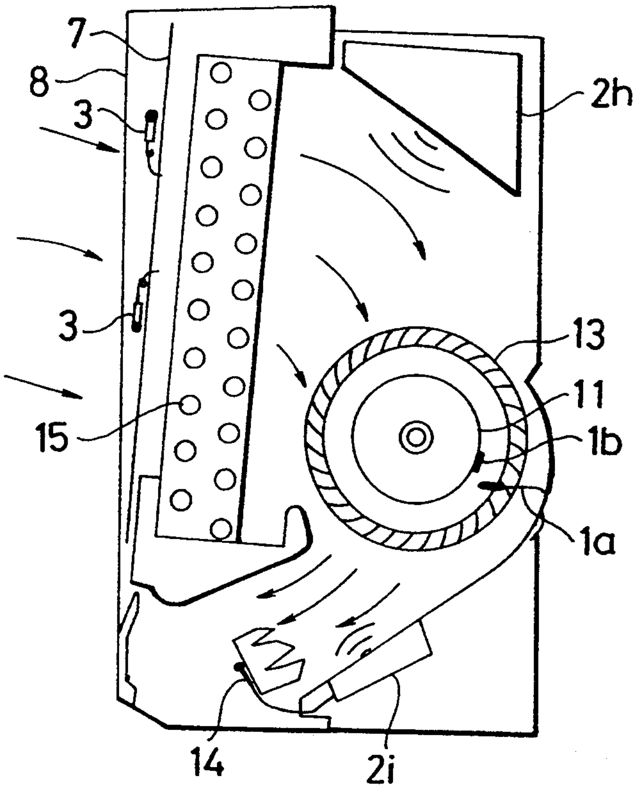
FIG. 15 is a sectional view showing an inside of the embodiment shown in FIG. 14.

FIG. 14 is a perspective view showing another embodiment of the air conditioner according to the present invention. FIG. 15 is a sectional view of this embodiment. In this embodiment, a rotation noise detecting pickup 1*a* for a cross flow fan and an electromagnetic noise pickup 16 for said motor 11 are provided, and a plurality of sound generating means 2*h* and 2*i* and a plurality of noise control effect detectig means 3 are provided. The plurality of sound generating means 2*h* and 2*i* are disposed in side by side relation at the positions as shown in FIG. 15 so that a stream is not obstructed thereby. A pickup 14 for detecting an air speed and an air pressure is disposed at the air outlet port, and a noise produced at the air outlet port is presupposed by processing and output signal of said pickup 14, thereby enabling the noise control by the sound generated from the sound generating means 2*i*. The noise control effect detecting means 3 are disposed at suitable positions of an inlet grill 8 having an air filter 7. The noise control effect detecting means may consist of a condenser microphone, with the object of lowering the cost and increasing the convenience in use. Although not shown in FIG. 15, the controller (phase converter) 4 is disposed at a position for easy maintenance, as in the case of the electrical control box 9. The control arrangement of this embodiment may be the same as that shown in FIGS. 7 and 10.

The active noise control system according to the present invention may be applied to any air conditioner other than those described above and, furthermore, this system may be applied to an instrument other than the air conditioner.

Figure 16:
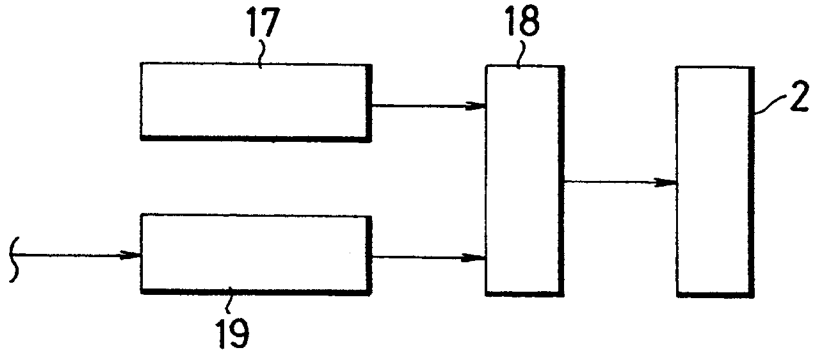
FIG. 16 shows an example of a circuit for producing a background music or the like from a sound generating means.

FIG. 16 illustrates a system in which a background music or a message is generated from the sound generating means 2. It is also possible to generate a cool sound at a room cooling state or a warm sound at a room heating state. Such sound is outputted from a signal outputting means 17 and fed through a mixer 18 to the sound generating means 2. A fixed filter or adaptive filter 19 is used.

In the air conditioner as described above, the plurality of sound generating means are disposed around the noise source at the distance shorter than ½ of the wavelength of the noise to be controlled and the respective sound generating means is fed with signals, separately, so that it is possible to control the noise over the wide range from the low frequency sound to high frequency sound. If a sound transmitting tube is used, it is possible to arrange the sound generating means at a position considerably remote from the noise source. In case of an air conditioner, the sound generating means are disposed at the positions where the air stream is not obstructed thereby, so that the performance of the air conditioner is not lowered. The sound generating means, or the like which are required to effect the active noise control can be disposed on the air inlet grill or in the space between the respective instruments, so that there is little restriction in arrangement of the instruments of the air conditioner.

Figure 17:
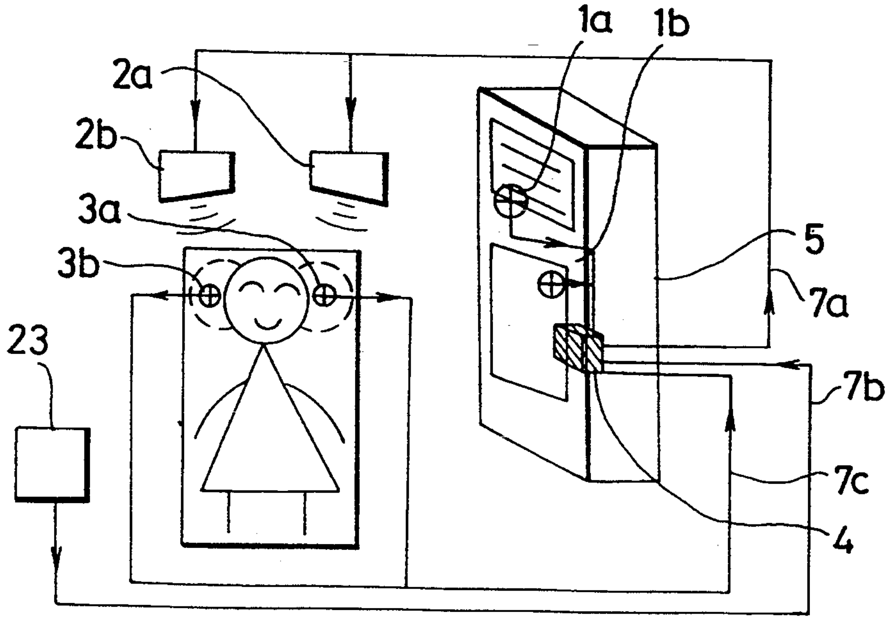
FIG. 17 illustrates an embodiment of the active noise control applied to an air conditioner.

FIG. 17 illustrates another embodiment of the invention. The apparatus shown in FIG. 17 includes noise detecting means 1*a* and 1*b* for detecting noises produced at an air outlet port and an air inlet port of an air conditioner, sound generating means 2*a* and 2*b* for generating sounds having opposite phase to that of the noise to be controlled, thereby actively controlling the noise, noise control effect detecting means 3*a* and 3*b* and a controller 4. The controller 4 acts to analyze the noise and cause the sound generating means 2*a* and 2*b* to produce sounds to effect active noise control. The respective instruments are connected together by parallel cords, coaxial cables, optical fibers or other conductors 7*a*, 7*b* and 7*c*, whereby the respective instruments can be set at freely selected positions and large amounts of information can be transmitted. In the embodiment shown in FIG. 17, two local areas near ears of a person are selected as two sound control areas and the noise control effect detecting means 3*a* and 3*b* are disposed at or near centers of the local noise control areas, whereby noises are controlled near the ears of the person to realize reduction of noises at these areas.

Figure 18:
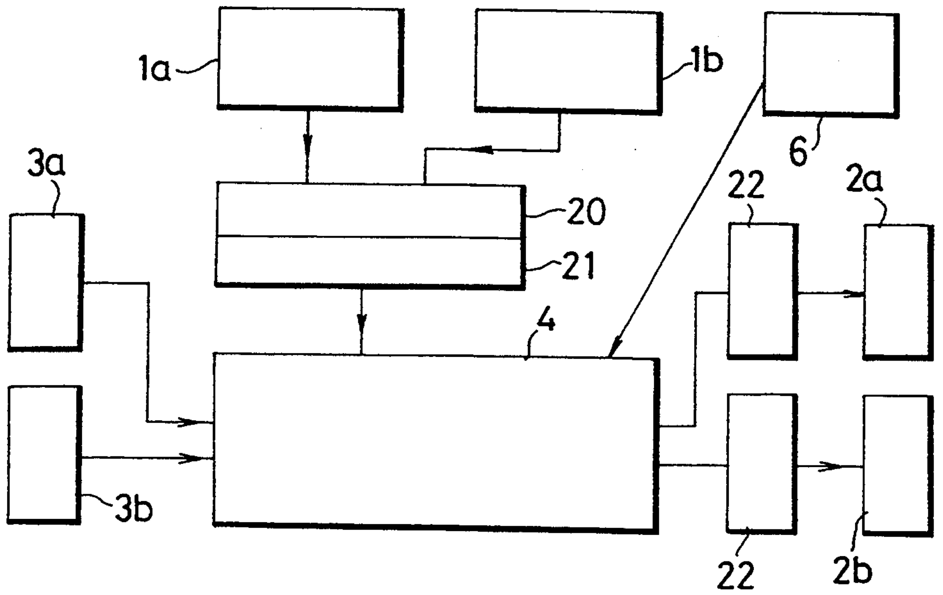
FIG. 18 is a diagram showing a connecting arrangement of the active noise control system as shown in FIG. 17.

FIG. 18 is a diagram showing a control system for effecting the active noise control. The noise detecting means 1*a* and 1*b* are disposed at an air outlet port and an air inlet port of an air conditioner to enable the arrangement to detect almost all of the noises produced from the air conditioner. Noise detecting signals are fed through a mixer 20 and a filter 21 to the controller 4 in the form of electric signals properly representing the noise produced by the air conditioner. The controller 4 acts to analyze and compute the electric signals representing the noise and the electric signals representing the sounds at the respective noise control areas detected by the noise control areas set near the two ears of the person, and to feed electric signals through power amplifiers 22 to the sound generating means 2*a* and 2*b*, which generate sounds which reduce sounds detected by the noise control effect detecting means 3*a* and 3*b*. A remote control unit 23 for the air conditioner may be directly connected to the controller 4, thereby effecting ON-OFF control. Sound such as background music may be generated at the same time from the sound generating means 2*a* and 2*b* and the generation of such sound may be turned ON or OFF by the above-mentioned remote control unit. In the above embodiment, condenser microphones are used as the noise detecting means and the noise control effect detecting means.

Figure 19:
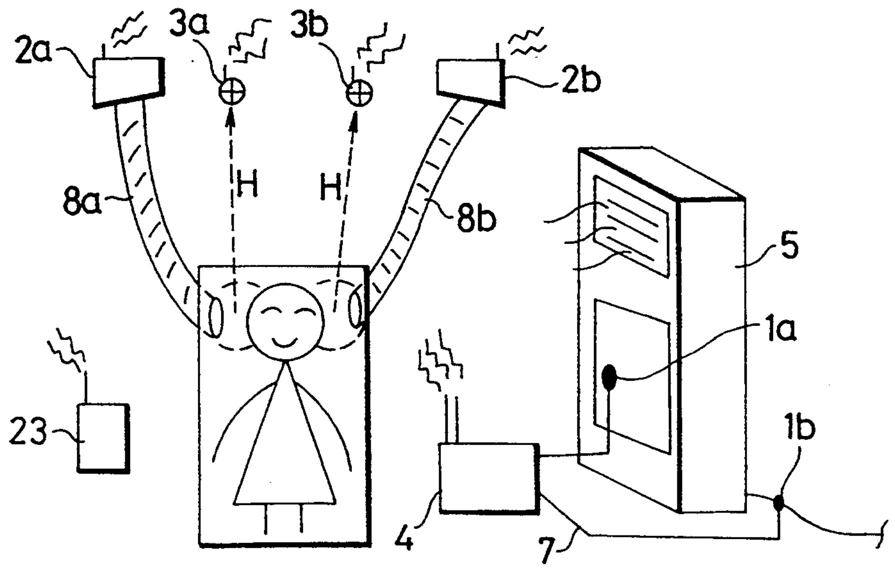
FIG. 19 illustrates another embodiment of the active noise control applied to an air conditioner.

FIG. 19 illustrates an embodiment in which in order to control noise near two noise control areas near ears of a person, noise control effect detecting means 3*a* and 3*b* are disposed at positions remote from said noise control areas and actually measured values of transfer functions between the noise control effect detecting means and the ears of the person are previously set in the controller 4, thereby detecting the noise control effect at the noise control areas near the ears of the person. The sounds radiated from the sound generating means 2*a* and 2*b* are transmitted through hollow tubes 8*a* and 8*b* or the like to optimum positions relative to the noise control areas near the ears, whereby it is possible to locate the sound generating means at desired remote positions.

Figure 20:
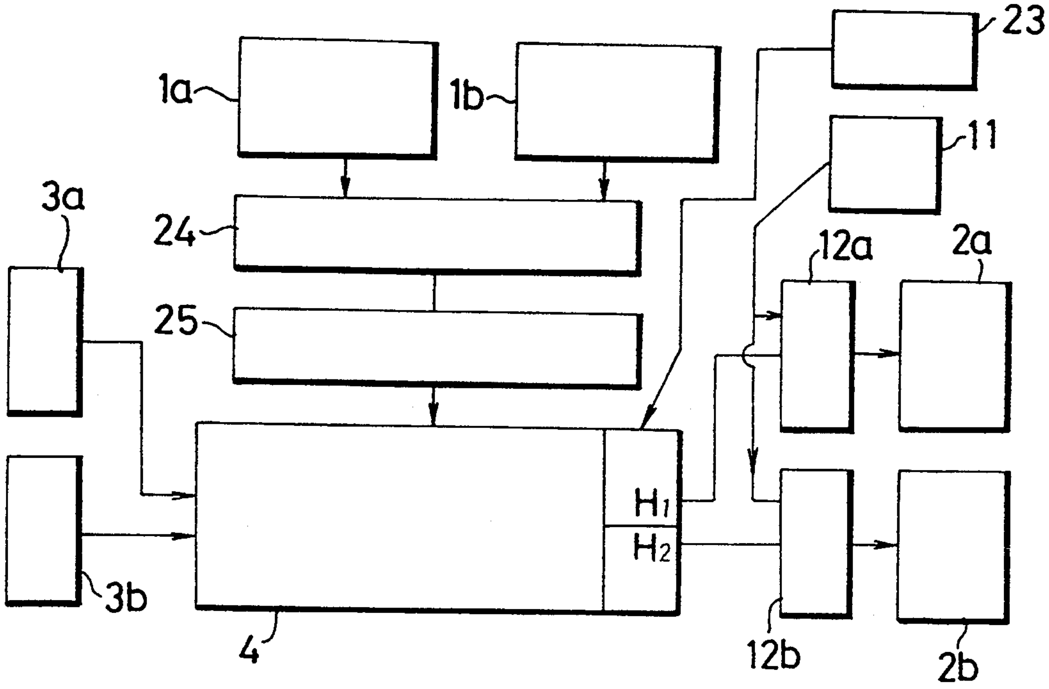
FIG. 20 is a diagram of a connecting arrangement of the active noise control system of the embodiment shown in FIG. 19.

FIG. 20 is a diagram showing a control system for effecting the active noise control as shown in FIG. 19. The signals detected by the noise control effect detecting means 1*a* and 1*b* are fed through a signal processing circuit 24, which produces a component corresponding n times (usually 1–4 times) of a wavelength of said signal, a mixer and filter 25, whereby an electric signal properly representing the noise of the air conditioner, and said electric signal is fed to the controller 4. The controller 4 acts to effect analysis and computation on the basis of the above-mentioned electric signals and the signals fed from said noise control effect detecting means 3*a* and 3*b*, to produce electric signals to be fed to the sound generating means 2*a* and 2*b* to generate the noise control sounds to reduce the output signals from the noise control effect detecting means 3*a* and 3*b*. Then, the electric signals are fed through filters 25 which have actually measured values H1 and H2 of the transfer functions between the areas near the ears and the noise control effect detecting means 3*a* and 3*b*, whereby said electric signals are corrected to the electric signals which enable sound control at the areas near the ears and fed to the sound generating means 2*a* and 2*b*. Power amplifiers are contained in the sound generating means 2*a* and 2*b*, so that it is possible to cause the sound generating means 2*a* and 2*b* to generate compact and satisfactory sounds. It is possible to cause the sound generating means 2*a* and 2*b* to generate a background music, a message, a comfortable sound, a cool sound at the room cooling time, a warm sound at the room heating time or the like, and in order to generate such sound, an output signal of a signal transmitting means 26 and a signal from the controller 4 are fed through mixers 12*a* and 12*b* to sound generating means 2*a* and 2*b*. As in the embodiment shown in FIG. 19, a remote control unit 23 may be used to effect remote ON-OFF control.

Figure 21:
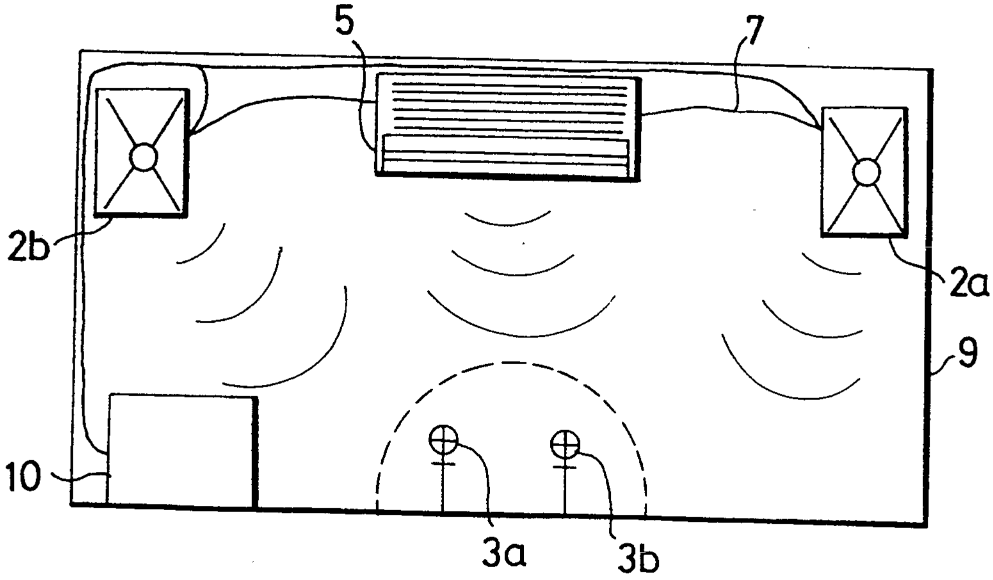
FIG. 21 illustrates another embodiment of the active noise control according to the present invention applied to an air conditioner.

FIG. 21 illustrates an embodiment in which an active noise control apparatus according to the present invention is applied to a room 9 which is already equipped with another sound generating system 10 (for example, a stereo music system) including loudspeakers 2*a* and 2*b* and driver system therefore. By connecting the active noise control system as described above with said system 10, the noise radiating from the air conditioner 5 can be controlled in active manner in a local area indicated by a broken line. The sound generating means for active noise control can be disposed at an area outside of the air conditioner 5 and, therefore, the another sound generating means 2*a* and 2*b* which are already equipped in the room 9 can be utilized as the sound generating means for the active noise control, and thus the required cost can be lowered. The noise control effect detecting means 3*a* and 3*b* are mounted in local areas to be noise controlled. It is possible to dispose the noise control effect detecting means 3*a* and 3*b* at any desired positions in the room 9 only by changing the transfer functions between the noise control effect detecting means 3*a* and 3*b* and the sound generating means 2*a* and 2*b* which is to be introduced into filters in the controller, thereby selecting the noise control areas as desired.

Figure 22:
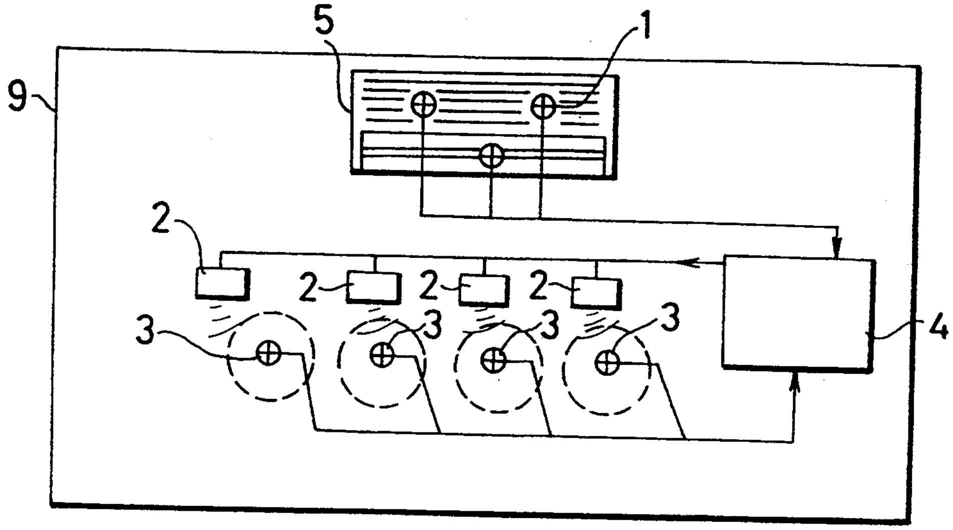
FIG. 22 illustrates a further embodiment of the active noise control according to the present invention applied to an air conditioner.

FIG. 22 illustrates an embodiment in which a plurality of noise control areas are formed in a room 9 by using a plurality of sound generating means 2, a plurality of noise control effect detecting means 3 and a multi-channel controller 4 for active noise control. According to this embodiment, the active noise control can be realized on plural persons in the room 9. Each of the noise control areas is separately subjected to the active noise control by the sound generating means which is located at a nearest position to the respective noise control areas. The controller 4 may be located at a position inside or outside of the air conditioner 5 and can be interchangeable, so that it is possible to select any channel number for noise control. In this embodiment, in the respective noise control areas indicated by a broken line, it is possible to provide the noise control areas at any desired positions by displaying the plurality of sound generating means 2 and the plurality of noise control effect detecting means 3 and changing the corresponding transfer functions in the filter in the controller 4. It is also possible to use a plurality of noise detecting means 1 to precisely and effectively detect the noises radiated from the air conditioner.

Figure 23:
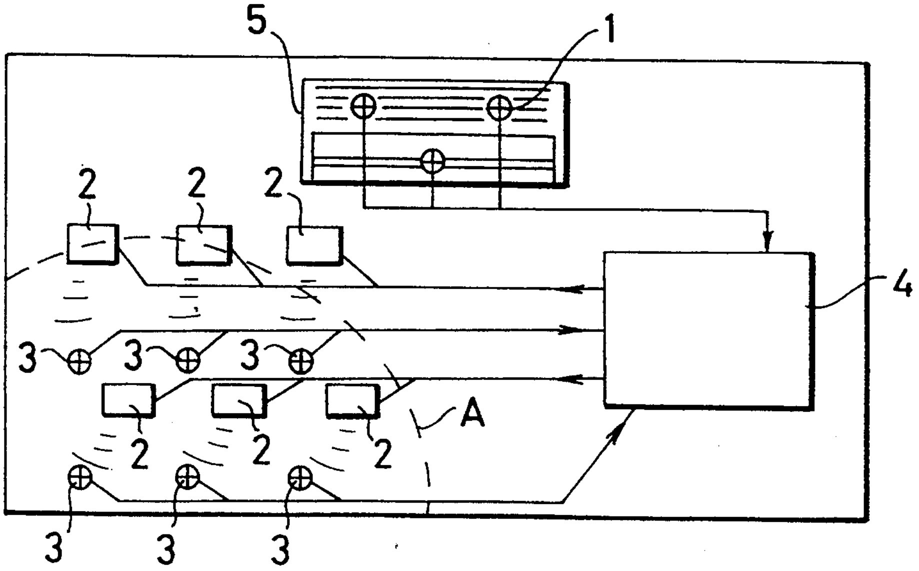
FIG. 23 illustrates another embodiment of the invention applied to an air conditioner.
Figure 24:
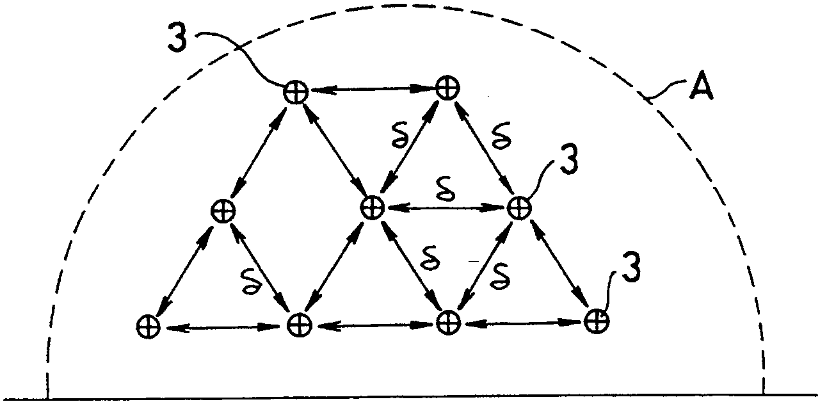
FIG. 24 is a diagram showing a distance relation between a plurality of noise control effect detecting means.

FIG. 23 illustrates an embodiment in which a larger noise control area indicated by a broken line is formed by assembly of a plurality of noise control areas. In FIG. 23, a plurality of noise control effect detecting areas 3 are assembled at predetermined distances to form a large area indicated by A. The plurality of noise control effect detecting means 3 are assembled in the manner as indicated in FIG. 24. A size of a noise control area is proportional to a wavelength of a noise to be controlled. Accordingly, if it is assumed that a frequency of a noise to be controlled is f, a distance δ between the noise control effect detecting means 3 is determined to meet the following formula (1) (which means that δ is within ½ of wavelength of a noise to be controlled) or the following formula (2) (which means that δ is within ⅓ or a wavelength of a noise to be controlled):

$$\delta < \frac{170}{f} \quad (1)$$

$$\delta < \frac{113}{f} \quad (2)$$

and the noise control effect detecting means are disposed in the area A accordingly. If it is desired to suppress only x (db) in noise level, the distance between the noise control effect detecting means 3 is determined by the following formula (3):

$$\delta < \frac{y}{f} \times 0.6^{x/10} \quad (3)$$

In this formula, f is a wavelength of a noise to be controlled and y is an index indicating a control precision of an algorithm in the controller 4. ($0<y<1$, y approaches 1 as the control precision is higher). The location of the sound generating means 2 is not limited to any specific position, but it is desirable to locate the sound generating means to a position nearer to the corresponding sound control effect detecting means 3 within or near the noise control area A. This is because, in the area other than the noise control area, in general, a noise is increased owing to interference of sounds and the noise is decreased in or near the noise control area.

Figure 25:
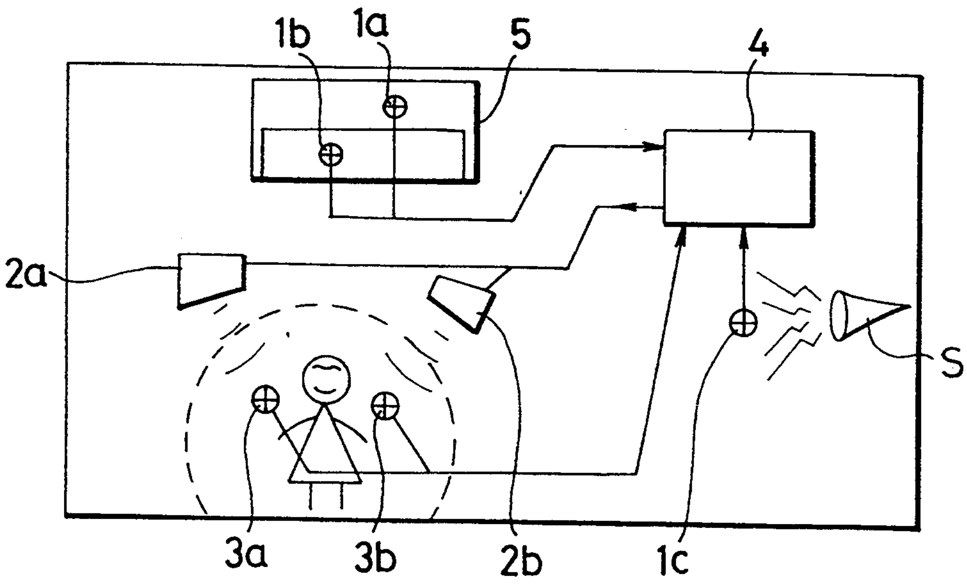
FIG. 25 illustrates another embodiment of the active noise control according to the present invention.

FIG. 25 illustrates an embodiment in which another noise source S exists in addition to the air conditioner 5. In this embodiment, an additional noise detecting means 1*c* is provided and the noise other than that produced from said another noise source is controlled at the same time of the noise control of the air conditioner, by connecting said noise detecting means 1*c* to a controller 4.

According to the above system, it is possible to decide the positions, the numbers or the sizes of the noise control areas as desired and to enable the convenient use of spaces in a room for the noise control effect detecting means and the sound generating means.

What is claimed is:

1. An active noise control apparatus for a three-dimensional space including a noise detecting means for detecting a noise radiated from a noise source, a control device for controlling an active noise control, a plurality of sound generating means and a plurality of noise control effect detecting means, said sound generating means being disposed at positions surrounding said noise source with distances between said noise source and each sound generating means and between respective sound generating means being shorter than ½ of a wavelength of a maximum frequency of a noise to be controlled, said control device for active noise control being arranged to cause said sound generating means to radiate a sound wave having an opposite phase to and a same sound pressure, same wavelength and same directivity as those of a noise having a wide frequency range radiated from said noise source into a three-dimensional space, on a basis of output signals of said noise detecting means and said noise control effect detecting means.

2. An active noise control apparatus according to claim 1, wherein at least one of said plurality of sound generating means has a sound transmitting tube for transmitting a sound from said sound generating means, and said sound transmitting tube is disposed at a position where a sound radiating position of the sound transmitting tube is located to satisfy the requirement defined as above.

3. An active noise control apparatus according to claim 1 or 2, further comprising fixed filters interposed between at least a portion of said plurality of sound generating means and said control device and between at least a portion of said plurality of noise control effect detecting means and said control device, respectively, said fixed filters having a characteristic determined on a basis of actually measured values of transfer functions between said sound generating means and a representative spot in said three-dimensional space and transfer functions between said noise control effect detecting means and said representative spot in said three-dimensional space.

4. An active noise control apparatus according to claim 3, further comprising at least one adaptive filter interposed between at least a portion of said plurality of sound generating means and said control device and between at least a portion of said plurality of noise control effect detecting means and said control device, respectively, said at least one adaptive filter having characteristics corresponding to said transfer functions and making variations on a basis of output signals of said noise detecting means and said noise control effect detecting means.

5. An active noise control apparatus according to claim 3, wherein said plurality of noise control effect detecting means are located at positions where a sound pressure produced by interference of sounds coming from said noise source and said sound generating means becomes minimum.

6. An active noise control apparatus according to claim 3, further comprising fixed filters interposed between at least a portion of said noise detecting means and said control device, said fixed filter having a characteristic which is determined on a basis of transfer functions between said noise detecting means and said representative spot in said three-dimensional space.

7. An active noise control apparatus according to claim 3, wherein said noise source exists in an air conditioner and said noise detecting means, said control device for active noise control, said sound generating means and said noise control effect detecting means are disposed in said air conditioner.

8. An active noise control apparatus according to claim 7, wherein said plurality of sound generating means are disposed at positions where an air stream flowing through the air conditioner is not obstructed thereby.

9. An active noise control apparatus according to claim 1, further comprising fixed filters interposed between further comprising at least a portion of said noise detecting means and said control device, said fixed filter having a characteristic which is determined on a basis of transfer functions between said noise detecting means and a representative spot in said three-dimensional space.

10. An active noise control apparatus according to claim 9, further comprising at least one adaptive filter interposed between at least a portion of said noise detecting means and said control device, said at least one adaptive filter having characteristics corresponding to transfer functions between said noise detecting means and a representative spot in said three-dimensional space and making variations on a basis of output signals of said noise detecting means and said noise control effect detecting means.

11. An active noise control apparatus according to claim 9, wherein said plurality of noise control effect detecting means are located at positions where a sound pressure produced by interference of sounds coming from said noise source and said sound generating means becomes minimum.

12. An active noise control apparatus according to claim 9, wherein said noise source exists in an air conditioner and said noise detecting means, said control device for active noise control, said sound generating means and said noise control effect detecting means are disposed in said air conditioner.

13. An active noise control apparatus according to claim 12, wherein said plurality of sound generating means are disposed at positions where an air stream flowing through the air conditioner is not obstructed thereby.

14. An active noise control apparatus according to claim 1, wherein said noise source exists in an air conditioner and said noise detecting means, and said control device for active noise control, said sound generating means and said noise control effect detecting means are disposed in said air conditioner.

15. An active noise control apparatus according to claim 14, wherein said plurality of sound generating means are disposed at positions where an air stream flowing through the air conditioner is not obstructed thereby.

16. An active noise control apparatus according to claim 1, further comprising at least one adaptive filter interposed between at least a portion of said noise detecting means and said control device, said having characteristics corresponding to transfer functions between said noise detecting means and a representative spot in said three-dimensional space and making variations on a basis of output signals of said noise detecting means and said noise control effect detecting means.

17. An active noise control apparatus according to claim 16, wherein said plurality of noise control effect detecting means are located at positions where a sound pressure produced by interference of sounds coming from said noise source and said sound generating means becomes minimum.

18. An active noise control apparatus according to claim 16, wherein said noise source exists in an air conditioner and said noise detecting means, said control device for active noise control, said sound generating means and said noise control effect detecting means are disposed in said air conditioner.

19. An active noise control apparatus according to claim 18, wherein said plurality of sound generating means are disposed at positions where an air stream flowing through the air conditioner is not obstructed thereby.

20. An active noise control apparatus including a noise detecting means, a sound generating means for active noise control, a noise control effect detecting means disposed at a local noise control area to detect a sound within said noise control area and a control device for active noise control, said control device for active noise control being arranged to control said sound generating means to effect an active noise control to cause a sound reaching said noise control area from said sound generating means detected by said noise control effect detecting means to become minimum under an action of a sound having an opposite phase to and same sound pressure and same wavelength as those of noise to be controlled, on a basis of detecting output signals fed from said noise detecting means and said noise control effect detecting means;

wherein at lease one of said control device and noise detecting means are disposed inside a noise producing unit which generates a noise to be controlled and said sound generating means and said noise control effect detecting means are disposed outside of said noise producing unit, and said control device for active noise control and said noise control effect detecting means are connected together by signal transmitting means including at least one of flexible and movable parallel cords, coaxial cables, optical fibers and radio waves.

21. An active noise control apparatus according to claim 20, further comprising at least one adaptive filter interposed between at least a portion of said noise detecting means and said control device, said at least one adaptive further having a characteristic which is determined on a basis of transfer functions between said noise detecting means and a representative spot in a three-dimensional space and making variations on a basis of output signals of said noise detecting means and said noise control effect detecting means.

22. An active noise control apparatus according to claim 20, wherein a plurality of sound generating means are provided, and a plurality of noise control effect detecting means are located at local noise control areas in a three-dimensional space.

23. An active noise control apparatus according to claim 22, wherein said noise source exists in an air conditioner and said noise detecting means are located in said air conditioner.

24. An active noise control apparatus according to claim 20, wherein a plurality of sound generating means are provided and a plurality of noise control effect detecting means are disposed separately in local noise control areas.

25. An active noise control apparatus according to claim 24, wherein said noise source exists in an air conditioner and said noise detecting means are located in said air conditioner.

26. An active noise control apparatus according to claim 20, wherein said sound generating means and said control device for active noise control are connected together by signal transmitting means including at least one of flexible and movable parallel cords, coaxial cables, optical fibers and radio waves.

27. An active noise control apparatus according to claim 20, wherein sound transmitting tubes are provided to conduct sounds for active noise control radiated by said sound generating means from any position into said three-dimensional space.

28. An active noise control apparatus according to claim 20, wherein said noise source exists in an air conditioner and said noise detecting means are located in said air conditioner.

29. An active noise control apparatus according to claim 20, further comprising fixed filters interposed between at least a portion of said plurality of sound generating means and said control device and between at least a portion of said plurality of noise control effect detecting means and said control device, respectively, said fixed filters having a characteristic determined on a basis of actually measured values of transfer functions between said sound generating means and a representative spot in a three-dimensional space and transfer functions between said noise control effect detecting means and said representative spot in said three-dimensional space.

30. An active noise control apparatus according to claim 20, further comprising fixed filters interposed between at least a portion of said noise detecting means and said control device, said fixed filter having a characteristic which is determined on a basis of transfer functions between said noise detecting means and a representative spot in a three-dimensional space.

31. An active noise control apparatus including a noise detecting means, a sound generating means for active noise control, a noise control effect detecting means disposed at a local noise control area to detect a sound within said noise control area and a control device for active noise control, said control device for active noise control being arranged to control said sound generating means to effect an active noise control to cause a sound reaching said noise control area from said sound generating means detected by said noise control effect detecting means to become minimum under an action of a sound having an opposite phase to and same sound pressure and same wavelength as those of noise to be controlled, on a basis of detecting output signals fed from said noise detecting means and said noise control effect detecting means;

wherein at lease one of said control device and noise detecting means are disposed inside a noise producing unit which generates a noise to be controlled and said sound generating means and said noise control effect detecting means are disposed outside of said noise producing unit, and said control device for active noise control and said noise control effect detecting means are connected together by signal transmitting means including at least one of flexible and movable parallel cords, coaxial cables, optical fibers and radio waves, wherein a plurality of sound generating means are provided, and a plurality of noise control effect detecting means are located at local noise control areas in a three-dimensional space, and wherein said plurality of noise control effect detecting means are disposed at distances shorter than one half to one third of a wavelength of a noise to be controlled and said plurality of local noise control areas are arranged to be assembled together to form a large local noise control area surrounding said noise control effect detecting means.

32. An active noise control apparatus according to claim 31, wherein said sound generating means and said control device for active noise control are connected together by signal transmitting means including at least one of flexible and movable parallel cords, coaxial cables, optical fibers and radio waves.

33. An active noise control apparatus according to claim 31, wherein sound transmitting tubes are provided to conduct sounds for active noise control radiated by said sound generating means from any position into said three-dimensional space.

34. An active noise control apparatus according to claim 31, wherein the noise source exists in an air conditioner and the noise detecting means are located in said air conditioner.

35. An active noise control apparatus according to claim 31, further comprising fixed filters interposed between at least a portion of said plurality of sound generating means and said control device and between at least a portion of said plurality of noise control effect detecting means and said control device, respectively, said fixed filters having a characteristic determined on a basis of actually measured values of transfer functions between said sound generating means and a representative spot in said three-dimensional space and transfer functions between said noise control effect detecting means and said representative spot in said three-dimensional space.

36. An active noise control apparatus according to claim 31, further comprising fixed filters interposed between at least a portion of said noise detecting means and said control device, said fixed filter having a characteristic which is determined on a basis of transfer functions between said noise detecting means and a representative spot in said three-dimensional space.

37. An active noise control apparatus according to claim 31, further comprises at least one adaptive filter interposed between at least a portion of said noise detecting means and said control device, said at least one adaptive filter having a characteristic which is determined on a basis of transfer functions between said noise detecting means and a representative spot in said three-dimensional space and making variations on a basis of output signals of said noise detecting means and said noise control effect detecting means are used to replace at least a portion of a function of said at least one adaptive filters.

* * * * *